(12) United States Patent
Edwards

(10) Patent No.: US 11,406,748 B2
(45) Date of Patent: Aug. 9, 2022

(54) DUAL LUMEN CANNULA WITH EXPANDABLE LUMEN

(71) Applicant: CardiacAssist, Inc., Pittsburgh, PA (US)

(72) Inventor: Kelli Edwards, Glenshaw, PA (US)

(73) Assignee: CardiacAssist, Inc, Pittsburgh, PA (US)

( * ) Notice: Subject to any disclaimer, the term of this patent is extended or adjusted under 35 U.S.C. 154(b) by 345 days.

(21) Appl. No.: 16/799,230

(22) Filed: Feb. 24, 2020

(65) Prior Publication Data
US 2021/0260265 A1    Aug. 26, 2021

(51) Int. Cl.
*A61M 1/36* (2006.01)
*A61M 1/26* (2006.01)
*A61M 1/16* (2006.01)
*A61M 25/00* (2006.01)

(52) U.S. Cl.
CPC ........ *A61M 1/3659* (2014.02); *A61M 1/1698* (2013.01); *A61M 1/267* (2014.02); *A61M 1/3666* (2013.01); *A61M 1/3667* (2014.02); *A61M 25/0026* (2013.01); *A61M 2025/0025* (2013.01)

(58) Field of Classification Search
CPC .... A61M 1/1689; A61M 1/267; A61M 1/285; A61M 1/3659; A61M 1/3667; A61M 25/00; A61M 25/0026; A61M 2025/0023; A61M 2025/0024; A61M 2025/0025; A61M 2025/0031
See application file for complete search history.

(56) References Cited

U.S. PATENT DOCUMENTS

| | | | | |
|---|---|---|---|---|
| 4,406,656 A | * | 9/1983 | Hattler | A61M 25/0009 604/523 |
| 5,807,311 A | * | 9/1998 | Palestrant | A61M 25/003 604/537 |
| 6,508,777 B1 | * | 1/2003 | Macoviak | A61M 1/3659 604/9 |

(Continued)

FOREIGN PATENT DOCUMENTS

| WO | 2015139031 A1 | 9/2015 |
|---|---|---|
| WO | 2016054543 A1 | 4/2016 |

OTHER PUBLICATIONS

International Search Report and Written Opinion dated May 12, 2021 for International Application No. PCTUS2021019031.

*Primary Examiner* — Philip R Wiest
(74) *Attorney, Agent, or Firm* — Seager, Tufte & Wickhem LLP

(57) ABSTRACT

A dual lumen drainage cannula configured for use in a VA ECMO system includes a first drainage tube having a proximal end, a distal end, and at least one aperture in at least one wall of the first drainage tube proximate to the distal end of the first drainage tube, and a second drainage tube having a proximal end, a distal end, and at least one aperture in at least one wall of the second drainage tube proximate to the distal end of the second drainage tube. The first drainage tube passes through the second drainage tube. The dual lumen drainage cannula also includes a sleeve positioned adjacent to an interior wall of the second drainage tube. The sleeve is formed of a flexible material so as to be expandable and collapsible within the second drainage tube.

20 Claims, 7 Drawing Sheets

(56) References Cited

U.S. PATENT DOCUMENTS

| | | | |
|---|---|---|---|
| 6,808,510 B1* | 10/2004 | DiFiore | A61M 25/0069 604/523 |
| 6,935,344 B1* | 8/2005 | Aboul-Hosn | A61M 1/3653 128/898 |
| 7,879,003 B2 | 2/2011 | Bertolero et al. | |
| 9,168,352 B2* | 10/2015 | Kelly | A61M 25/007 |
| 2003/0036727 A1* | 2/2003 | Schock | A61M 60/135 604/509 |
| 2005/0085761 A1* | 4/2005 | Wang | A61M 1/3653 604/4.01 |
| 2006/0184099 A1* | 8/2006 | Hong | A61M 25/0023 604/43 |
| 2011/0004197 A1* | 1/2011 | Sansoucy | B29C 48/10 264/166 |
| 2011/0295236 A1* | 12/2011 | Gregory | A61M 25/1018 604/540 |
| 2012/0209221 A1* | 8/2012 | Patterson | A61M 25/0021 604/523 |
| 2013/0261605 A1* | 10/2013 | Gregersen | A61M 25/0009 156/303.1 |
| 2017/0035987 A1 | 2/2017 | Ardehali | |

* cited by examiner

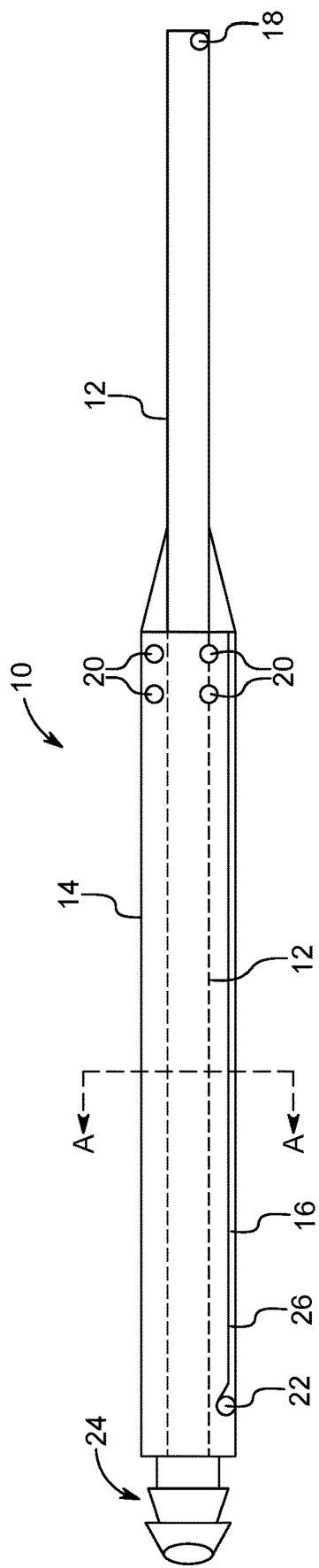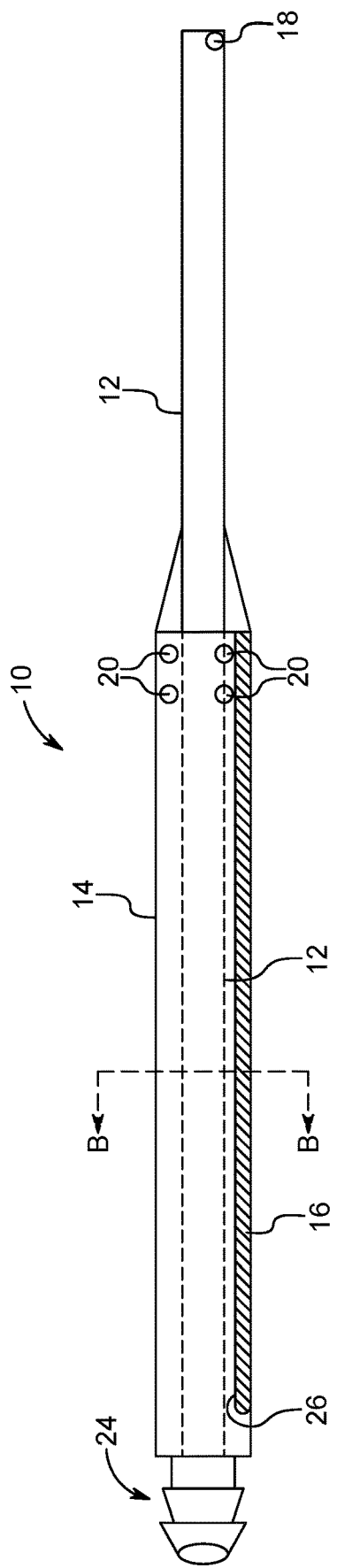

DUAL LUMEN CANNULA WITH EXPANDABLE LUMEN

BACKGROUND

Field

The present disclosure generally relates to devices and methods for assisting a patient's heart with a cannula. More specifically, the present disclosure is related to cannula assemblies, systems including at least one cannula assembly, and methods of use thereof for medical procedures such as veno-arterial extracorporeal membrane oxygenation.

Description of the Related Art

Veno-arterial extracorporeal membrane oxygenation (VA ECMO) is one method for treating right ventricular failure, respiratory failure, and/or cardiac failure percutaneously. A VA ECMO procedure draws blood from the venous circulation and pumps it through an oxygenator and back into the arterial circulation via the femoral artery. VA ECMO bypasses the lungs and the heart completely, elevating arterial pressure and infusing blood into the arterial system with added oxygen and reduced carbon dioxide.

In conventional VA ECMO systems, one drainage cannula is placed in the superior vena cava (SVC), interior vena cava (IVC), right atrium region by way of a femoral vein (typically) to drain blood therefrom, and a separate, second return cannula is placed in an artery to return oxygenated (and cleansed of carbon dioxide) blood at a higher pressure. In conventional VA ECMO systems, the drainage of additional blood from the pulmonary artery requires the insertion of a second drainage cannula (third total cannula) into the pulmonary artery by way of the jugular vein or other access site. Among the benefits of drawing blood from both the right atrium and the pulmonary artery is that the drained blood is fully mixed venous blood, including coronary circulation, which drains into the right atrium, and further that the right ventricle is unloaded to a greater extent. However, the use of multiple cannulas consequently requires multiple cannula insertion sites, thereby increasing the risk of bleeding, vessel damage, and infection, as well as pain and discomfort to the patient.

SUMMARY

In view of the foregoing, there exists a need for a dual lumen cannula, particularly for use in VA ECMO procedures, capable of draining blood from multiple vascular locations while allowing for the modulation of blood flow through at least one of the lumens, or tubes, supplying the drained blood to a pump. Embodiments of the present disclosure are generally directed to a VA ECMO system, a cannula assembly for a VA ECMO system, and a method of providing VA ECMO of a heart.

Embodiments of the present disclosure are directed to a veno-arterial extracorporeal membrane oxygenation (VA ECMO) system including a dual lumen drainage cannula. The dual lumen drainage cannula includes a first drainage tube having a proximal end, a distal end, and at least one aperture defined in at least one wall of the first drainage tube proximate to the distal end of the first drainage tube. The dual lumen drainage cannula also includes a second drainage tube having a proximal end, a distal end, and at least one aperture defined in at least one wall of the second drainage tube proximate to the distal end of the second drainage tube, wherein the first drainage tube passes through the second drainage tube, and wherein the distal end of the second drainage tube is coupled to a portion of the first drainage tube between the proximal end and the distal end of the first drainage tube. The dual lumen drainage cannula also may include a sleeve positioned adjacent to an interior wall of the second drainage tube, wherein at least one wall of the sleeve is formed of a flexible material so as to be expandable and collapsible within the second drainage tube.

In some embodiments, the dual lumen drainage cannula also includes a port formed on an exterior wall of the second drainage tube, wherein the port is in communication with the sleeve.

In some embodiments, the port is located adjacent to the proximal end of the second drainage tube.

In some embodiments, the sleeve extends from the port to the distal end of the second drainage tube.

In some embodiments, the sleeve is sized and configured to receive at least one element therein so as to allow for expansion of the sleeve.

In some embodiments, the at least one element is at least one flexible rod.

In some embodiments, the at least one element is a fluid.

In some embodiments, the dual lumen drainage cannula further includes a secondary sleeve positioned adjacent to an interior sidewall of the first drainage tube, wherein at least one wall of the secondary sleeve is formed of a flexible material so as to be expandable and collapsible within the first drainage tube.

In some embodiments, the dual lumen drainage cannula further includes a secondary port formed on an exterior wall of the second drainage tube, wherein the secondary port is in communication with the secondary sleeve.

In some embodiments, the at least one aperture of the first drainage tube is configured for draining blood from a pulmonary artery of a patient, and the at least one aperture of the second drainage tube is configured for draining blood from a right atrium of the patient.

In some embodiments, the first drainage tube extends coaxially relative to the second drainage tube.

Other embodiments of the present disclosure are directed to a veno-arterial extracorporeal membrane oxygenation (VA ECMO) system. The system includes a dual lumen drainage cannula. The dual lumen drainage cannula includes a first drainage tube having a proximal end, a distal end, and at least one aperture defined in at least one wall of the first drainage tube proximate to the distal end of the first drainage tube. The dual lumen drainage cannula also includes a second drainage tube having a proximal end, a distal end, and at least one aperture defined in at least one wall of the second drainage tube proximate to the distal end of the second drainage tube, wherein the first drainage tube passes through the second drainage tube, and wherein the distal end of the second drainage tube is coupled to a portion of the first drainage tube between the proximal end and the distal end of the first drainage tube. The dual lumen drainage cannula may also include a sleeve positioned adjacent to an interior wall of the second drainage tube, wherein at least one wall of the sleeve is formed of a flexible material so as to be expandable and collapsible within the second drainage tube. The system may further include a blood pump having an inlet connected to an outlet of the dual lumen drainage cannula, an oxygenator connected to an outlet of the blood pump, and an infusion cannula connected to an outlet of the oxygenator and configured for insertion into the vasculature of a patient.

In some embodiments, the dual lumen drainage cannula further includes at least one port formed on an exterior wall of the second drainage tube, wherein the at least one port is in communication with the sleeve.

In some embodiments, the sleeve is sized and configured to receive at least one element therein so as allow for expansion of the sleeve.

In some embodiments, the at least one element includes at least one flexible rod.

In some embodiments, the at least one element includes a fluid.

In some embodiments, the system further includes a fluid source and a controller, wherein the fluid source is configured to automatically expand or collapse the at least one wall of the sleeve based on instructions received from the controller.

Other embodiments of the present disclosure are directed to a method of providing veno-arterial extracorporeal membrane oxygenation (VA ECMO) of a heart. The method includes providing a dual lumen drainage cannula. The dual lumen drainage cannula includes a first drainage tube having a proximal end, a distal end, and at least one aperture defined in at least one wall of the first drainage tube proximate to the distal end of the first drainage tube. The dual lumen drainage cannula also includes a second drainage tube having a proximal end, a distal end, and at least one aperture defined in at least one wall of the second drainage tube proximate to the distal end of the second drainage tube, wherein the first drainage tube passes through the second drainage tube, and wherein the distal end of the second drainage tube is coupled to a portion of the first drainage tube between the proximal end and the distal end of the first drainage tube. The dual lumen drainage cannula may also include a sleeve positioned adjacent to an interior wall of the second drainage tube, wherein at least one wall of the sleeve is formed of a flexible material so as to be expandable and collapsible within the second drainage tube. The method may include inserting the dual lumen drainage cannula into a first site in a patient's vasculature. The method may also include maneuvering the dual lumen drainage cannula through the patient's vasculature such that the distal end of the first drainage tube is at least within proximity of the patient's pulmonary artery and such that the distal end of the second drainage tube is at least within proximity of the patient's right atrium. The method may include draining blood through the first drainage tube and the second drainage tube to a blood pump, pumping drained blood through an oxygenator to reduce carbon dioxide content of the blood, and delivering oxygenated blood with reduced carbon dioxide content to a second site in the patient's vasculature.

In some embodiments, the dual lumen drainage cannula further includes at least one port formed on an exterior wall of the second drainage tube and configured to be in communication with the sleeve, and the method includes inserting at least one element into the sleeve via the port so as to expand the sleeve within the second drainage tube.

In some embodiments, inserting at least one element into the sleeve includes one of inserting at least one flexible rod into the sleeve and inserting a fluid into the sleeve.

Further embodiments of the present disclosure are set forth in the following numbered clauses.

Clause 1. A dual lumen drainage cannula configured for use in a veno-arterial extracorporeal membrane oxygenation (VA ECMO) system, the dual lumen drainage cannula comprising: a first drainage tube having a proximal end, a distal end, and at least one aperture defined in at least one wall of the first drainage tube proximate to the distal end of the first drainage tube; a second drainage tube having a proximal end, a distal end, and at least one aperture defined in at least one wall of the second drainage tube proximate to the distal end of the second drainage tube, wherein the first drainage tube passes through the second drainage tube, and wherein the distal end of the second drainage tube is coupled to a portion of the first drainage tube between the proximal end and the distal end of the first drainage tube; and a sleeve positioned adjacent to an interior wall of the second drainage tube, wherein at least one wall of the sleeve is formed of a flexible material so as to be expandable and collapsible within the second drainage tube.

Clause 2. The dual lumen drainage cannula according to clause 1, further comprising a port formed on an exterior wall of the second drainage tube, wherein the port is in communication with the sleeve.

Clause 3. The dual lumen drainage cannula according to clause 1 or 2, wherein the port is located adjacent to the proximal end of the second drainage tube.

Clause 4. The dual lumen drainage cannula according to any of clauses 1 to 3, wherein the sleeve extends from the port to the distal end of the second drainage tube.

Clause 5. The dual lumen drainage cannula according to any of clauses 1 to 4, wherein the sleeve is sized and configured to receive at least one element therein so as allow for expansion of the sleeve.

Clause 6. The dual lumen drainage cannula according to any of clauses 1 to 5, wherein the at least one element is at least one flexible rod.

Clause 7. The dual lumen drainage cannula according any of clauses 1 to 6, wherein the at least one element is a fluid.

Clause 8. The dual lumen drainage cannula according to any of clauses 1 to 7, further comprising a secondary sleeve positioned adjacent to an interior sidewall of the first drainage tube, wherein at least one wall of the secondary sleeve is formed of a flexible material so as to be expandable and collapsible within the first drainage tube.

Clause 9. The dual lumen drainage cannula according to any of clauses 1 to 8, further comprising a secondary port formed on an exterior wall of the second drainage tube, wherein the secondary port is in communication with the secondary sleeve.

Clause 10. The dual lumen drainage cannula according to any of clauses 1 to 9, wherein the at least one aperture of the first drainage tube is configured for draining blood from a pulmonary artery of a patient, and wherein the at least one aperture of the second drainage tube is configured for draining blood from a right atrium of the patient.

Clause 11. The dual lumen drainage cannula according to any of clauses 1 to 10, wherein the first drainage tube extends coaxially relative to the second drainage tube.

Clause 12. A veno-arterial extracorporeal membrane oxygenation (VA ECMO) system comprising: a dual lumen drainage cannula comprising: a first drainage tube having a proximal end, a distal end, and at least one aperture defined in at least one wall of the first drainage tube proximate to the distal end of the first drainage tube, a second drainage tube having a proximal end, a distal end, and at least one aperture defined in at least one wall of the second drainage tube proximate to the distal end of the second drainage tube, wherein the first drainage tube passes through the second drainage tube, and wherein the distal end of the second drainage tube is coupled to a portion of the first drainage tube between the proximal end and the distal end of the first drainage tube, and a sleeve positioned adjacent to an interior wall of the second drainage tube, wherein at least one wall of the sleeve is formed of a flexible material so as to be expandable and collapsible within the second drainage tube; a blood pump having an inlet connected to an outlet of the dual lumen drainage cannula; an oxygenator connected to an outlet of the blood pump; and an infusion cannula connected to an outlet of the oxygenator and configured for insertion into the vasculature of a patient.

Clause 13. The VA ECMO system according to clause 12, wherein the dual lumen drainage cannula further comprises at least one port formed on an exterior wall of the second drainage tube, wherein the at least one port is in communication with the sleeve.

Clause 14. The VA ECMO system according to clause 12 or 13, wherein the sleeve is sized and configured to receive at least one element therein so as allow for expansion of the sleeve.

Clause 15. The VA ECMO system according to any of clauses 12 to 14, wherein the at least one element comprises at least one flexible rod.

Clause 16. The VA ECMO system according to any of clauses 12 to 15, wherein the at least one element comprises a fluid.

Clause 17. The VA ECMO system according to any of clauses 12 to 16, further comprising a fluid source and a controller, wherein the fluid source is configured to automatically expand or collapse the at least one wall of the sleeve based on instructions received from the controller.

Clause 18. A method of providing veno-arterial extracorporeal membrane oxygenation (VA ECMO) of a heart, the method comprising: providing a dual lumen drainage cannula comprising: a first drainage tube having a proximal end, a distal end, and at least one aperture defined in at least one wall of the first drainage tube proximate to the distal end of the first drainage tube, a second drainage tube having a proximal end, a distal end, and at least one aperture defined in at least one wall of the second drainage tube proximate to the distal end of the second drainage tube, wherein the first drainage tube passes through the second drainage tube, and wherein the distal end of the second drainage tube is coupled to a portion of the first drainage tube between the proximal end and the distal end of the first drainage tube, and a sleeve positioned adjacent to an interior wall of the second drainage tube, wherein at least one wall of the sleeve is formed of a flexible material so as to be expandable and collapsible within the second drainage tube; inserting the dual lumen drainage cannula into a first site in a patient's vasculature; maneuvering the dual lumen drainage cannula through the patient's vasculature such that the distal end of the first drainage tube is at least within proximity of the patient's pulmonary artery and such that the distal end of the second drainage tube is at least within proximity of the patient's right atrium; draining blood through the first drainage tube and the second drainage tube to a blood pump; pumping drained blood through an oxygenator to reduce carbon dioxide content of the blood; and delivering oxygenated blood with reduced carbon dioxide content to a second site in the patient's vasculature.

Clause 19. The method of clause 18, wherein the dual lumen drainage cannula further comprises at least one port formed on an exterior wall of the second drainage tube and configured to be in communication with the sleeve, and wherein the method comprises inserting at least one element into the sleeve via the port so as to expand the sleeve within the second drainage tube.

Clause 20. The method of clause 18 or 19, wherein inserting at least one element into the sleeve comprises one of inserting at least one flexible rod into the sleeve and inserting a fluid into the sleeve.

Further details and advantages of the present disclosure will be understood from the following detailed description read in conjunction with the accompanying drawings.

BRIEF DESCRIPTION OF THE DRAWINGS

FIG. 1 is a side view of a drainage cannula according to an embodiment of the present disclosure;

FIG. 2 is another side view of the drainage cannula of FIG. 1, according to an embodiment of the present disclosure;

DETAILED DESCRIPTION

Figure 3:
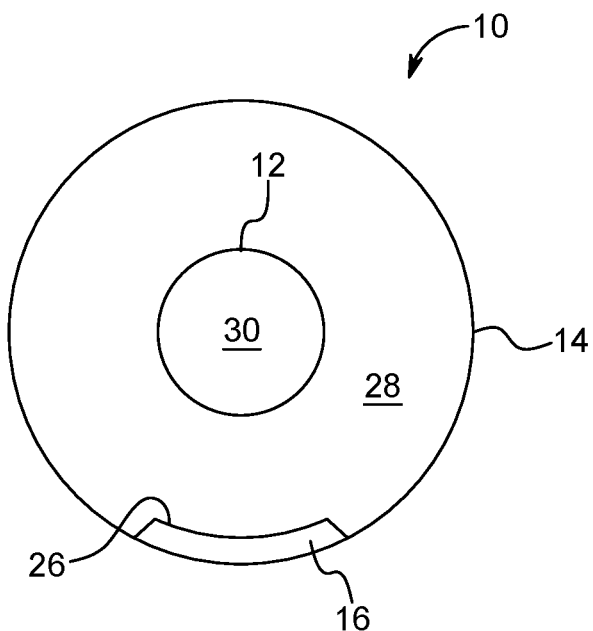
FIG. 3 is a cross-sectional view of the drainage cannula along line A-A of FIG. 1, according to an embodiment of the present disclosure.

For purposes of the description hereinafter, the terms "end," "upper," "lower," "right," "left," "vertical," "horizontal," "top," "bottom," "lateral," "longitudinal," and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments or aspects. Hence, specific dimensions and other physical characteristics related to the embodiments or aspects disclosed herein are not to be considered as limiting.

As used herein, the term "at least one of" is synonymous with "one or more of". For example, the phrase "at least one of A, B, and C" means any one of A, B, and C, or any combination of any two or more of A, B, and C. For example, "at least one of A, B, and C" includes one or more of A alone; or one or more B alone; or one or more of C alone; or one or more of A and one or more of B; or one or more of A and one or more of C; or one or more of B and one or more of C; or one or more of all of A, B, and C. Similarly, as used herein, the term "at least two of" is synonymous with "two or more of". For example, the phrase "at least two of D, E, and F" means any combination of any two or more of D, E, and F. For example, "at least two of D, E, and F" includes one or more of D and one or more of E;

or one or more of D and one or more of F; or one or more of E and one or more of F; or one or more of all of D, E, and F.

When used in relation to a cannula, catheter, or other device inserted into a patient, the term "proximal" refers to a portion of such device farther from the end of the device inserted into the patient. When used in relation to a cannula, catheter, or other device inserted into a patient, the term "distal" refers to a portion of such device nearer to the end of the device inserted into the patient.

Referring to the drawings, in which like reference characters refer to like parts throughout the several views thereof, various embodiments of a dual lumen drainage cannula 10 (hereinafter referred to as "the drainage cannula 10") are shown. With initial reference to FIG. 1, the assembled drainage cannula 10, according to one embodiment, generally includes a first drainage lumen, or drainage tube, 12 having a first length and a second drainage tube 14 having a second length. The first length of the first drainage tube 12 is greater than the second length of the second drainage tube 14. It is to be understood that the first length of the first drainage tube 12 and the second length of the second drainage tube 14, as shown in FIG. 1, are not to scale, with each being truncated for the purposes of illustration. For example, the first drainage tube 12 may have a working length of, e.g., approximately 40-45 cm, while the working length of second drainage tube 14 may be shorter (e.g., approximately 30 cm), dependent upon the desired application and placement of the cannula 10, the size/age of the patient, etc. Furthermore, while first drainage tube 12 and second drainage tube 14 are each shown and described herein as having substantially cylindrical shapes, it is to be understood that the first drainage tube 12 and second drainage tube 14 are not limited to such a cylindrical shape, and may have any appropriate and clinically-functional cross-sectional shape.

The first drainage tube 12 is disposed partially within the second drainage tube 14. In some embodiments, the first drainage tube 12 and the second drainage tube 14 may be arranged coaxially with one another about the central axis. However, in some embodiments, the first drainage tube 12 and second drainage tube 14 are not arranged coaxially, as the first drainage tube 12 may be offset from the central axis defined by the second drainage tube 14. While not shown, it is to be understood that one or more support structures may be provided within second drainage tube 14 so as to support and guide first drainage tube 12 therein.

An inner diameter of the second drainage tube 14 may be greater than an outer diameter of the first drainage tube 12 such that a flow cavity is formed inside the second drainage tube 14 around a portion of the first drainage tube 12 disposed within the second drainage tube 14. The first drainage tube 12 and the second drainage tube 14 are fluidly separated from one another along the entire length of the first drainage tube 12, such that a first fluid (e.g., blood drained from the pulmonary artery of a patient) carried through the first drainage tube 12 does not mix with a second fluid (e.g., blood drained from the right atrium of the patient) carried through the second drainage tube 14 until the first fluid reaches a common proximal end of the first drainage tube 12 and the second drainage tube 14.

One or both of the first drainage tube 12 and the second drainage tube 14 may be manufactured from a medical-grade material such as, e.g., polyurethane. Alternatively, the lumens may be made from PVC or silicone, and may be dip molded, extruded, co-molded, or made using any other suitable manufacturing technique.

With continued reference to FIG. 1, at least one aperture 18 is provided proximate to a distal end of the first drainage tube 12. While FIG. 1 only illustrates one aperture 18, it is to be understood that a plurality of apertures 18 may be provided at the distal end of first drainage tube 12. In some embodiments, a plurality of apertures 18 may be arranged in a circular pattern extending around a circumference of the first drainage tube 12. In other embodiments, a plurality of apertures 18 may be disposed in multiple groups provided at various sites on the first drainage tube 12. Additionally and/or alternatively, the at least one aperture 18 may include an open hole on the distal end of the drainage tube 12, wherein the open hole is open in a direction substantially transverse to a central axis of the first drainage tube 12. In some embodiments, the first drainage tube 12 may include only an open hole functioning as an aperture 18.

Similarly, a plurality of apertures 20 may be provided proximate to a distal end of the second drainage tube 14. While a plurality of apertures 20 are shown in FIG. 1, it is to be understood that one or more apertures 20 may suffice. The plurality of apertures 20 are desirably arranged in a circular pattern extending around the outer circumference of the second drainage tube 14. In alternative embodiments, the plurality of drainage apertures 20 may be arranged in groups disposed at various sites along the length of the second drainage tube 14.

The aperture(s) 18 of the first drainage tube 12 are separated along the length of the drainage cannula 10 from the apertures 20 of the second drainage tube 14 by a given distance. In some embodiments, the distance between the aperture(s) 18 and the aperture(s) 20 may be, or may correspond to, a vascular distance between the right atrium and the pulmonary artery of the patient. In this way, the drainage cannula 10, when positioned in a patient for a VA ECMO procedure, may drain blood from the pulmonary artery via the aperture(s) 18 of the first drainage tube 12 and drain blood from the right atrium via the apertures 20 of the second drainage tube 14. The distance between the aperture(s) 18 and the aperture(s) 20 may vary based on the age and size of the patient, while the size and/or positioning of the aperture(s) 18 and the aperture(s) 20 may be selected based on desired flow rates during the VA ECMO procedure. In other embodiments, the distance between the aperture(s) 18 and the aperture(s) 20 may be, or may correspond to, a vascular distance between the right ventricle and the pulmonary artery of the patient such that the drainage cannula 10, when positioned in a patient for a VA ECMO procedure, may drain blood from the pulmonary artery via the aperture(s) 18 of the first drainage tube 12 and drain blood from the right ventricle via the aperture(s) 20 of the second drainage tube 14. In still further embodiments, the aperture(s) 20 may be positioned so as to drain blood from both the right atrium and the right ventricle simultaneously.

Referring still to FIG. 1, an outlet fitting 24 may be provided at the proximal end of the drainage cannula 10 for connecting the drainage cannula 10 to other medical devices such as, e.g., a blood pump. As shown in FIG. 1, the outlet fitting 24 may be formed as a male hose barb connector. However, it is to be understood that outlet fitting 24 is not limited to a barb connector, and may be any appropriate fitting such as, e.g., a luer connector, a male or female threaded connector, a continuation of the second drainage tube 14 configured to fit over a hose barb, etc.

The outlet fitting 24 is in fluid communication with both the first drainage tube 12 and the second drainage tube 14 such that the drainage cannula 10 defines only a single outlet for draining fluid from both the first drainage tube 12 and the second drainage tube 14. In this way, all flow in a proximal direction out of the drainage cannula 10 flows through the outlet fitting 24 to an appropriate common lumen, thereby eliminating the need for a secondary Y-connector in order for the first drainage tube 12 and the second drainage tube 14 to each drain to the same outlet.

While fluid is capable of simultaneous drainage from two different regions (e.g., the pulmonary artery and the right atrium) via the respective first drainage tube 12 and second drainage tube 14, in some instances, it may be desirable to modulate the flow of fluid from one area (e.g., the right atrium). In previous dual lumen cannula configurations, such modulation has been achieved by way of a Hoffman clamp applied near the proximal end of either lumen. However, as will be described further herein, and in accordance with embodiments of the present disclosure, the modulation of flow through at least the second drainage tube 14 in drainage cannula 10 may be achievable via an expandable lumen formed by a sleeve 16, which is expandable and collapsible so as to change the cross-sectional area of the second drainage tube 14, thereby allowing for a modulation of fluid flow through the second drainage tube 14.

With continued reference to FIG. 1, sleeve 16 is shown in a first configuration within the second drainage tube 14. Unlike first drainage tube 12 and second drainage tube 14, the interior of sleeve 16 is not fluid contacting (i.e., it does not carry blood). Instead, the at least one wall 26 of sleeve 16 is formed of a flexible material, thereby allowing the sleeve 16 to expand and/or collapse. The at least one wall 26 may be formed of any appropriate flexible material such as, e.g., thin-walled PVC, silicone, polyurethane, etc. Additionally, it is to be understood that the at least one wall 26 may be rounded or curved, flat, and/or rounded or curved in one portion and flat in another.

While termed as a "sleeve", it is to be understood that sleeve 16 is not configured to surround another structure, but instead defines a closed-end passage or opening for an element, or elements, to be inserted therein. While the flexible wall 26 may form one portion of the sleeve 16, other portions of the sleeve may be defined by, e.g., an interior wall of the second drainage tube 14.

The expansion or contraction of sleeve 16 may be manually or automatically controlled via a port 22. As will be described in further detail below, the port 22 allows entry and removal of one or more appropriate elements (i.e., a component or substance) capable of expanding the flexible sidewall(s) 26 of the sleeve 16.

Figure 4:
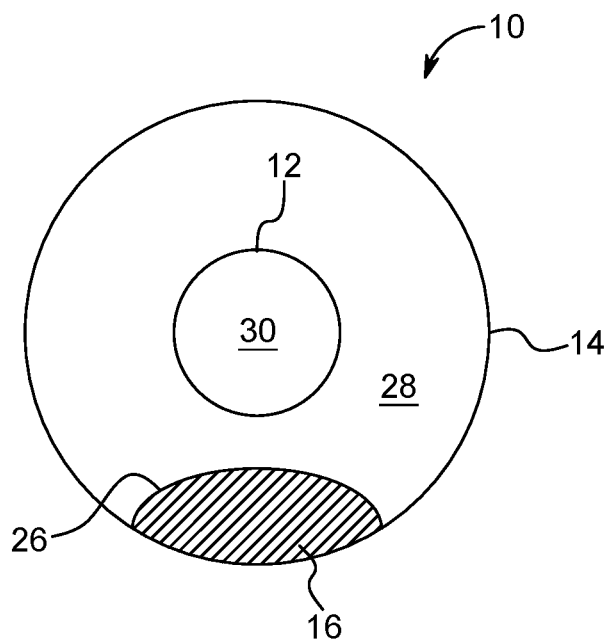
FIG. 4 is a cross-sectional view of the drainage cannula along line B-B of FIG. 2, according to an embodiment of the present disclosure.

In the configuration shown in FIG. 1, and also referring to the cross-sectional view shown in FIG. 3, the sleeve 16 is shown in a substantially collapsed position, wherein the at least one wall 26 is situated substantially adjacent the inner wall of the second drainage tube 14. In this configuration, the flow of fluid (i.e., blood) through the flow path 28 of second drainage tube 14 is substantially unaltered, as is the flow of fluid through the flow path 30 within first drainage tube 14. However, referring to FIGS. 2 and 4, when the at least one sidewall 26 of sleeve 16 is expanded, the sleeve 16 reduces the cross-sectional area of the flow path 28 of the second drainage tube 14, thereby modulating the flow of fluid through the second drainage tube 14. Accordingly, with the drainage cannula 10 according the present embodiment, the flow of fluid from one area (e.g., the right atrium) may be modulated during a drainage procedure. While FIGS. 2 and 4 illustrate that sleeve 16 takes on a substantially parabolic shape when in an expanded configuration, it is to be understood that sleeve 16 may be configured to achieve any other appropriate cross-sectional shapes when expanded.

As is shown in FIGS. 1 and 2, the port 22 in communication with the sleeve 16 is located substantially near the outlet fitting 24 of the drainage cannula 10. With such a configuration, the port 22 will be located well outside of the vasculature of the patient, and will be accessible to a practitioner, even when the drainage cannula 10 is in place within the vasculature. Furthermore, the sleeve 16 is shown as extending along a substantial length of the second drainage tube 14, originating from the port 22 and ending at or near the distal end of the second drainage tube 14. With this configuration, the total cross-sectional area of the flow path 28 that is reduced by the sleeve 16 is substantially constant along the length of the second drainage tube 14, thereby providing a consistent modulation of flow through the second drainage tube 14. However, in other embodiments, it is to be understood the sleeve 16 may extend less than the full length of the second drainage tube. Additionally, it is to be understood that the port 22 may be provided at other locations along the second drainage tube 14.

Figure 5:
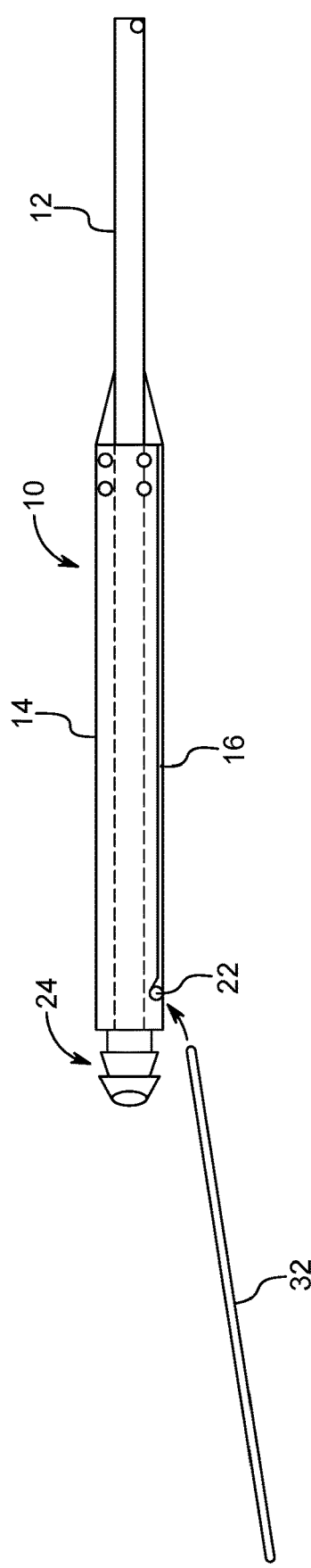
FIG. 5 is a side view of the drainage cannula of FIG. 1, illustrating a lumen expansion configuration in accordance with an embodiment of the present disclosure.
Figure 6:
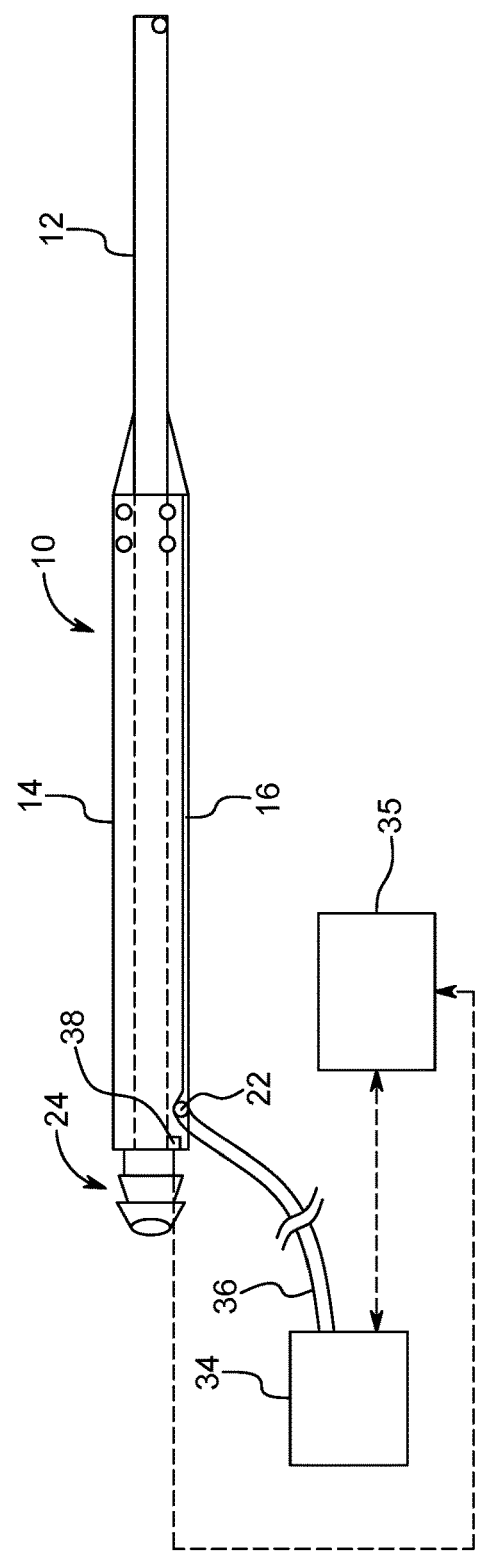
FIG. 6 is a side view of the drainage cannula of FIG. 1, illustrating a lumen expansion system in accordance with another embodiment of the present disclosure.

Next, with reference to FIGS. 5 and 6, various systems and methods of producing the expansion of sleeve 16 are illustrated in accordance with aspects of the present disclosure. Referring to FIG. 5, an element in the form of a flexible rod 32 is provided. The flexible rod 32 is capable of being fed into sleeve 16 via the port 22. As the flexible rod 32 is positioned within the sleeve 16, the sleeve 16 expands, thereby decreasing the cross-sectional area of the flow path of the second drainage tube 14, as described above with respect to FIGS. 1 and 2. The flexible rod 32 may be made of any appropriate medical-grade, flexible material such as, e.g., PVC, polyurethane, silicone, etc.

Prior to (or during) positioning of the drainage cannula 10 within the vasculature of the patient, the flexible rod 32 may be fed into sleeve 16 so as to modulate the flow of fluid through the second drainage tube 14, as described above. In some embodiments, a plurality of flexible rods 32 having varying diameters may be utilized, thereby enabling the practitioner to select an appropriately-sized flexible rod 32 for a desired level of fluid flow modulation. Additionally and/or alternatively, more than one flexible rod 32 may be utilized and fed into the sleeve 16, either sequentially or simultaneously, thereby providing for tunable levels of fluid flow modulation. In some embodiments, the overall length of each flexible rod 32 is at least as long as the sleeve 16, allowing the flexible rod(s) 32 to extend along the entire sleeve 16. However, it is to be understood that the flexible rod(s) 32 may be longer or shorter than the length of the sleeve 16.

Next, referring to FIG. 6, a system and method of producing the expansion of the sleeve 16 in accordance with another embodiment of the present disclosure is illustrated. Unlike the system and method described above with respect to FIG. 5, which utilizes flexible rod(s) 32 to expand the sleeve 16, the system and method of FIG. 6 utilizes a fluid to expand/inflate the sleeve 16. A fluid source 34 may be provided, with fluid source 34 operating to deliver the fluid to port 22 and cause the expansion and/or collapse of sleeve 16. In one embodiment, the fluid delivered by fluid source 34 is air or other gas. In another embodiment, the fluid delivered by the fluid source 34 is a liquid such as, e.g., saline.

The fluid source 34 may deliver the appropriate fluid to the sleeve 16 by way of a tube 36, with tube 36 being fitted to port 22 by any appropriate method providing a fluid-tight seal. Additionally, in some embodiments, the fluid source 34 may be configured to also draw fluid from the sleeve 16, thereby enabling the expansion of the sleeve 16 to be reversed or tuned by way of the fluid source 34. The fluid source 34 may be a manual or automated mechanism for producing fluid flow. For example, in some embodiments, fluid source 34 may be in communication, through either a wired or wireless connection, with a controller 35. Controller 35 may be any appropriate electronic controller, and may be configured to automatically control the fluid source 34 such that a desired amount of fluid is either provided to, or removed from, the sleeve 16.

In some embodiments, one or more sensors 38 may be provided within or adjacent to the drainage cannula 10, with the one or more sensors 38 being configurable to determine, e.g., flow rate through at least the second drainage tube 14. The one or more sensors 38 may communicate with the controller 35 through a wired or wireless connection. In this way, the controller 35 may provide instructions to the fluid source 34 to expand or collapse the wall(s) of the sleeve 16 based on, e.g., the flow rate of fluid passing through the second drainage tube 14. For example, if the fluid flow rate through second drainage tube 14 is higher than desired, the controller 35 may instruct the fluid source 34 to inflate/expand the sleeve 14 until the fluid flow rate reaches a desired level or falls below a predetermined threshold, which may be directly input by the practitioner and/or may be stored in a memory (not shown) of the controller 35. In this way, the controller 35 may be capable of continuously monitoring and adjusting the fluid flow rate through at least second drainage tube 14. While not shown, it is to be understood that one or more sensors 38 may also be capable of determining fluid flow rate through the first drainage tube 12. Accordingly, the controller 35 may be capable automatically modulating fluid flow through the second drainage tube 14 based on a desired flow ratio with the fluid flow through first drainage tube 12.

While the embodiments described above pertain to an automatically-controlled fluid source 34, in some embodiments, the fluid source 34 may be a manually-controlled source such as, e.g., a syringe. Thus, the fluid source 34 need not necessarily require the tube 36 in order to deliver and/or remove the fluid from the sleeve 16.

Figure 7:
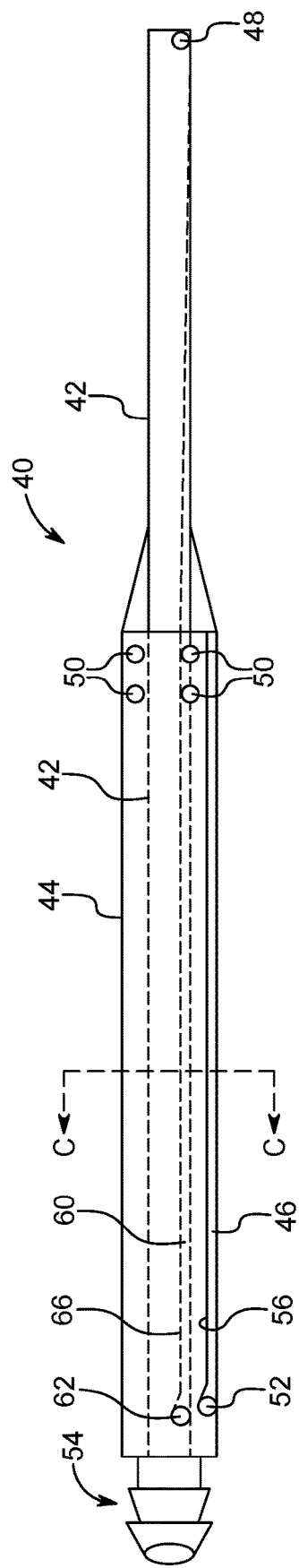
FIG. 7 is a side view of a drainage cannula according to another embodiment of the present disclosure.
Figure 8:
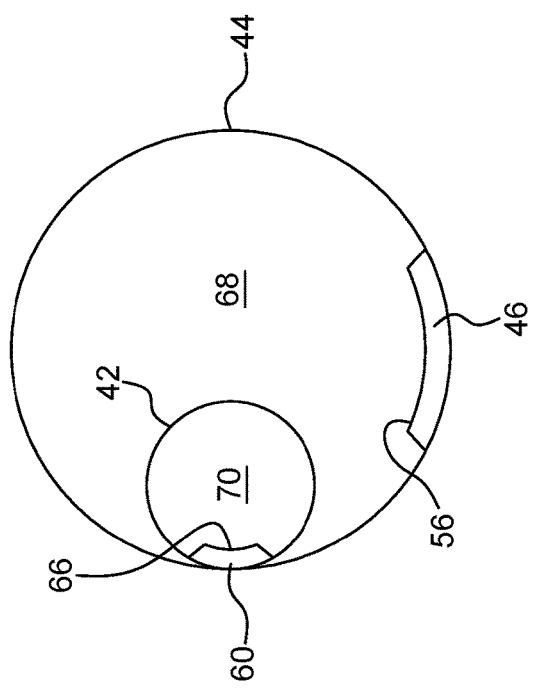
FIG. 8 is a cross-sectional view of the drainage cannula along line C-C of FIG. 7, according to an embodiment of the present disclosure.

Referring now to FIGS. 7 and 8, a drainage cannula 40 in accordance with another aspect of the disclosure is illustrated. While drainage cannula 10 described above with respect to FIGS. 1-6 only incorporates an expandable lumen (i.e., sleeve 16) into the flow path of the second drainage tube 14, drainage cannula 40 is configured to provide an expandable lumen within both a first drainage tube 42 and a second drainage tube 44. In this way, modulation of fluid flow through the first drainage tube 42, the second drainage tube 44, or both is possible.

The first drainage tube 42 of drainage cannula 40 is disposed partially within the second drainage tube 44. As shown in FIG. 7, the first drainage tube 42 and the second drainage tube 44 are arranged such that the first drainage tube 42 is offset from a central axis defined by the second drainage tube 44, with at least a portion of the first drainage tube 42 contacting an inner surface of the second drainage tube 44. The first drainage tube 42 and the second drainage tube 44 are fluidly separated from one another along the entire length of the first drainage tube 42, such that a first fluid (e.g., blood drained from the pulmonary artery of a patient) carried through the first drainage tube 42 does not mix with a second fluid (e.g., blood drained from the right atrium of the patient) carried through the second drainage tube 44 until the first fluid reaches a common proximal end of the first drainage tube 42 and the second drainage tube 44.

One or both of the first drainage tube 42 and the second drainage tube 44 may be manufactured from a medical-grade material such as, e.g., polyurethane. Alternatively, the tubes may be made from PVC or silicone, and may be dip molded, extruded, co-molded, or made using any other suitable manufacturing technique.

With continued reference to FIG. 7, at least one aperture 48 is provided proximate to a distal end of the first drainage tube 42. As with the at least one aperture 18 described above with respect to FIG. 1, the at least one aperture 48 may include an open hole at the distal end of the first drainage tube 42, wherein the open hole is open in a direction substantially transverse to a central axis of the first drainage tube 42. In some embodiments, the first drainage tube 12 may include only such an open hole functioning as an aperture 48. Similarly, a plurality of apertures 50 are provided proximate to a distal end of the second drainage tube 44. While a plurality of apertures 50 are shown in FIG. 7, it is to be understood that one or more apertures 50 may suffice. The plurality of apertures 50 are desirably arranged in a circular pattern extending around the outer circumference of the second drainage tube 44. In alternative embodiments, the plurality of drainage apertures 50 may be arranged in groups disposed at various sites along the length of the second drainage tube 44.

The aperture(s) 48 of the first drainage tube 42 are separated along the length of the drainage cannula 40 from the apertures 50 of the second drainage tube 44 by a given distance. In some embodiments, the distance between the aperture(s) 48 and the aperture(s) 50 may be, or may correspond to, a vascular distance between the right atrium and the pulmonary artery of the patient. In this way, the drainage cannula 40, when positioned in a patient for a VA ECMO procedure, may drain blood from the pulmonary artery via the apertures 48 of the first drainage tube 42 and drain blood from the right atrium via the apertures 50 of the second drainage tube 44. The distance between the aperture(s) 48 and the aperture(s) 50 may vary based on the age and size of the patient, while the size and/or positioning of the aperture(s) 48 and the aperture(s) 50 may be selected based on the desired flow rates during the VA ECMO procedure.

Referring still to FIG. 7, an outlet fitting 54 may be provided at the proximal end of the drainage cannula 40 for connecting the drainage cannula 40 to other medical devices such as, e.g., a blood pump. The outlet fitting 54 may be formed as any appropriate fitting such as, e.g., a barb connector, a luer connector, a male or female threaded connector, a continuation of the second drainage tube 44 configured to fit over a hose barb, etc. The outlet fitting 54 is in fluid communication with both the first drainage tube 42 and the second drainage tube 44 such that the drainage cannula 40 defines only a single outlet for draining fluid from both the first drainage tube 42 and the second drainage tube 44. In this way, all flow in a proximal direction out of the drainage cannula 40 flows through the outlet fitting 44 to an appropriate common lumen.

Similar to the second drainage tube 14 described above with respect to FIGS. 1-6, second drainage tube 44 includes a sleeve 46 capable of modulating flow through the second drainage tube 44. That is, the sleeve 46 is expandable so as to decrease the cross-sectional area of the second drainage tube 44, thereby decreasing fluid flow through the second drainage tube 44. The interior of sleeve 46 is not fluid contacting (i.e., it is not blood carrying), and at least one wall 56 of sleeve 46 is formed of a flexible material, thereby allowing the sleeve 46 to expand and/or contract, as is similarly described above with respect to sleeve 16. The at least one wall 56 may be formed of any appropriate flexible material such as, e.g., thin-walled PVC, silicone, polyurethane, etc. The expansion or contraction of sleeve 46 may be manually or automatically controlled via a port 52, with the port 52 allowing entry and removal of an appropriate component or substance (e.g., one or more rods, air, liquid, etc.) capable of expanding the flexible wall(s) 56 of the sleeve 46. In this way, the sleeve 46 may be expanded to reduce the cross-sectional area of a flow path 68 of the second drainage tube 44, thereby modulating the flow of fluid through the second drainage tube 44.

However, unlike drainage cannula 10 described above, in which only fluid flow through the second drainage cannula 14 is capable of being modulated, drainage cannula 40 shown in FIGS. 7 and 8 also includes a secondary sleeve 60 capable of modulating flow through the first drainage tube 42. Like the sleeve 46, the secondary sleeve 60 may be expandable so as to decrease the cross-sectional area of the first drainage tube 42, thereby decreasing fluid flow through the first drainage tube 42. At least one wall 66 of the secondary sleeve 60 is formed of a flexible material, thereby allowing the secondary sleeve 60 to expand and/or contract, as is similarly described above with respect to sleeves 16, 46. The at least one wall 66 may be formed of any appropriate flexible material such as, e.g., thin-walled PVC, silicone, polyurethane, etc.

The expansion or contraction of the secondary sleeve 60 may be manually or automatically controlled via a secondary port 62, which may be configured to allow entry and removal of an appropriate component or substance (e.g., one or more rods, air, liquid, etc.) capable of expanding the flexible wall(s) 66 of the secondary sleeve 60. In this way, the secondary sleeve 60 may be expanded to reduce the cross-sectional area of a flow path 70 of the first drainage tube 42, thereby modulating the flow of fluid through the first drainage tube 42.

As the first drainage tube 42 is positioned adjacent to a wall of the second drainage tube 44, as is shown in FIG. 8, the secondary port 62 allows the secondary sleeve 60 to be accessed via the second drainage tube 44 surrounding the first drainage tube 42. However, it is to be understood that other means of connecting secondary port 62 to the secondary sleeve 60 are possible (e.g., a tube passing between the secondary port 62 and the first drainage tube 42). Thus, the first drainage tube 42 need not necessarily be positioned adjacent a sidewall of the second drainage tube 44, and may even be positioned coaxially with the second drainage tube 44.

Furthermore, while FIGS. 7 and 8 show that drainage cannula 40 may include both a sleeve 46 and a secondary sleeve 60 for enabling the modulation of fluid flow through both the second drainage tube 44 and the first drainage tube 42, respectively, it is to be understood that the drainage cannula 40 may be configured such that only the first drainage tube 42 includes a flexible sleeve therein for the modulation of fluid flow.

Figure 9:
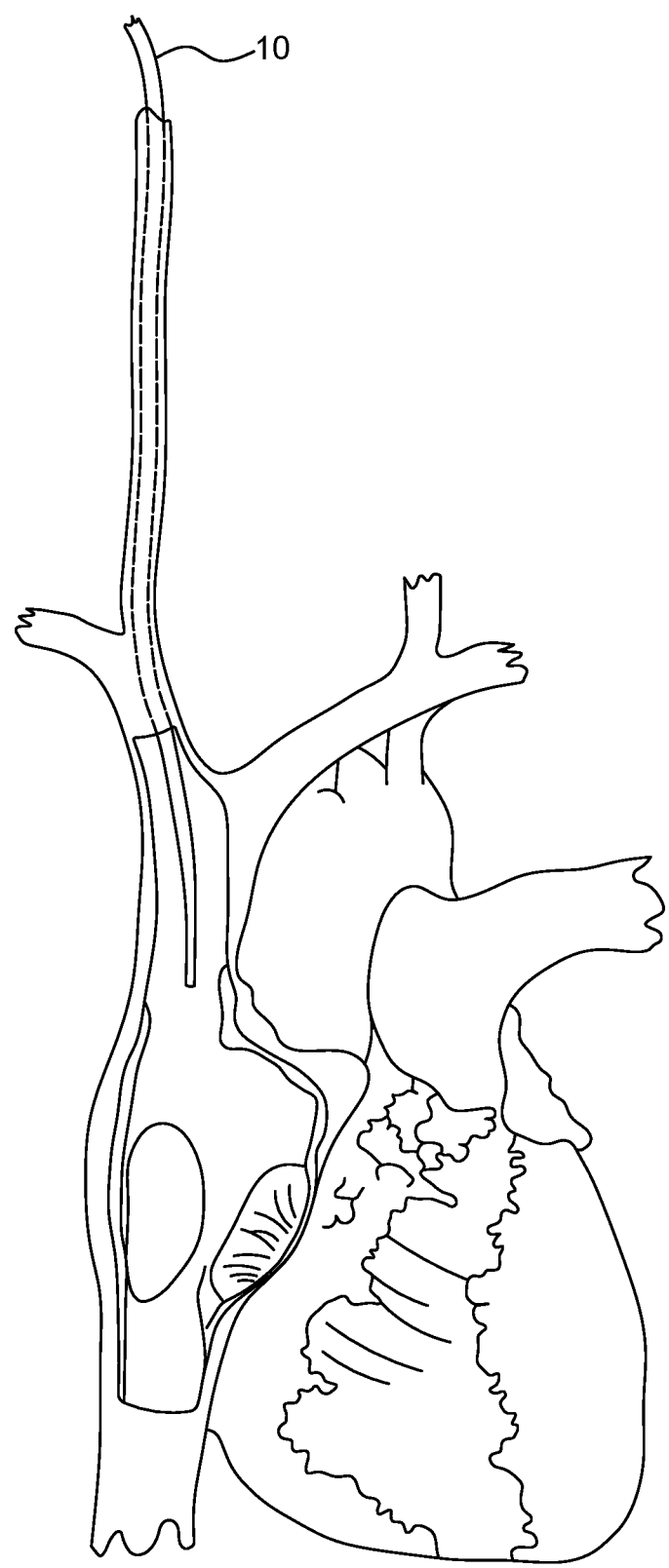
FIG. 9 is a schematic view of the drainage cannula of any of FIGS. 1-6 positioned in the superior vena cava of a body of a patient.
Figure 10:
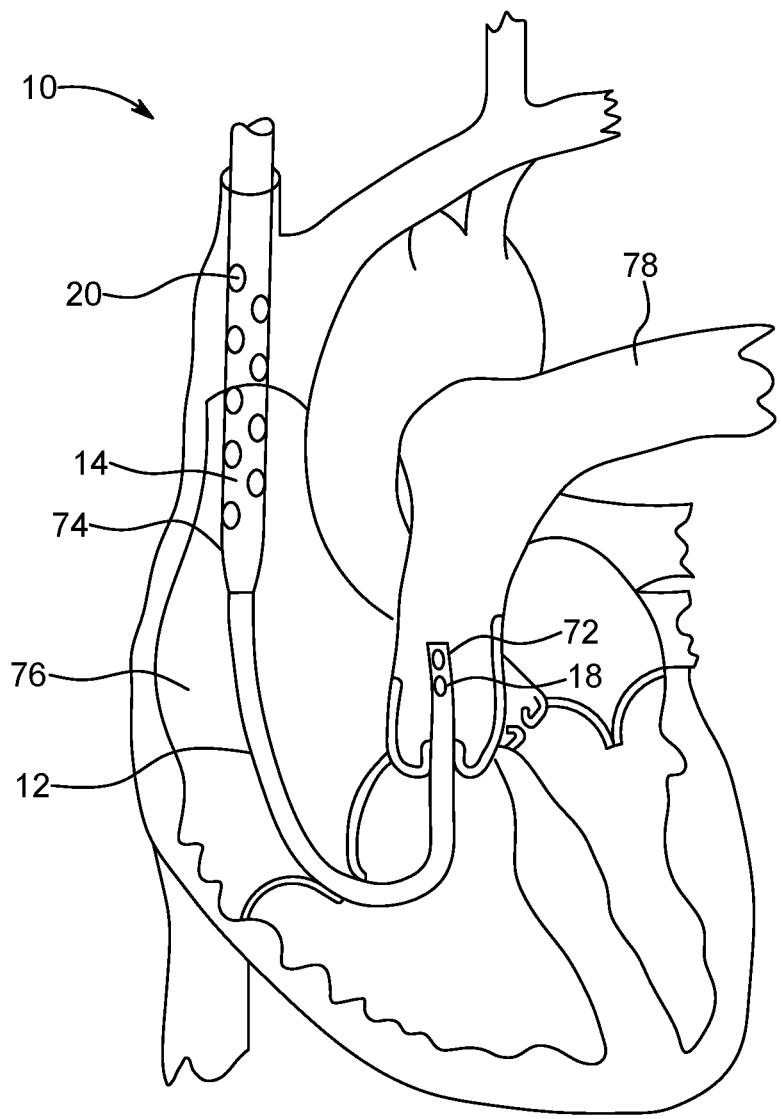
FIG. 10 is a schematic view of the drainage cannula of any of FIGS. 1-6 positioned inside a patient's heart.

Having described several non-limiting embodiments of the drainage cannula 10 above with respect to FIGS. 1-6, an exemplary and non-limiting method for supporting the right heart of a patient using the drainage cannula 10 will now be described with reference to FIGS. 9-10. In use, the drainage cannula 10 is inserted into the pulmonary artery in a percutaneous procedure. Initially, a percutaneous entry needle (not shown) is used to access the patient's internal jugular vein (IJV). An introducer, such as a guidewire, is then inserted through the needle until the tip of the introducer is positioned in the upper portion of the inferior vena cava/right atrium (IVC/RA) junction. The needle can then be removed and a pulmonary wedge catheter inserted over the guidewire into the pulmonary artery. The introducer tip is then threaded into the pulmonary artery, and the wedge catheter is removed. The IJV is then serially dilated and the drainage cannula 10 is threaded along the introducer into the IJV, through the right ventricle, and into the pulmonary artery. The first distal end 72 of the first drainage tube 12 is sufficiently flexible so as to navigate the IJV, right ventricle, and pulmonary artery. The drainage cannula 10 may include insertion depth markers and radiopaque markers for aiding the user in placing the drainage cannula 10 in the right atrium. Once the position of the drainage cannula 10 is acceptable, the introducer may be removed and the drainage cannula 10 may clamped in place. For example, the drainage cannula 10 may be secured to the patient's neck using a suture. FIG. 10 shows the drainage cannula 10 positioned in the patient according to some embodiments of the disclosure. In particular, the second distal end 74 is positioned at least within proximity with the right atrium 76, while the first distal end 72 extends into the pulmonary artery 78.

Figure 11:
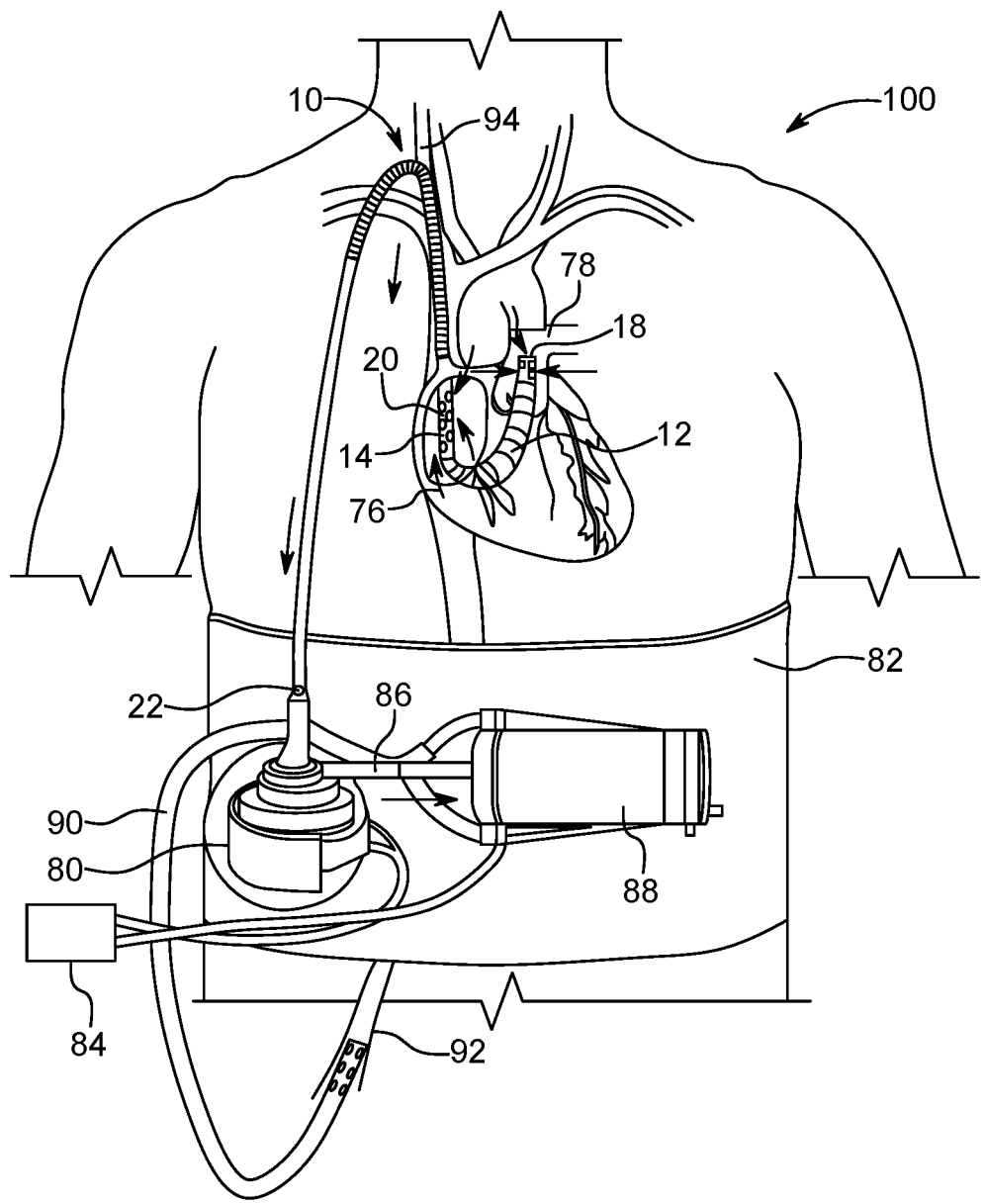
FIG. 11 is a schematic view of a VA ECMO system, including the drainage cannula of any of FIGS. 1-6, according to an embodiment of the present disclosure.

Referring now to FIG. 11, the drainage cannula 10 is shown schematically as part of a VA ECMO system 100. As described above with reference to FIGS. 9 and 10, the first drainage tube 12 is positioned such that the plurality of apertures 18 thereof are located in the pulmonary artery 78, thereby allowing blood from the pulmonary artery 78 to drain through the plurality of apertures 18 and into the first drainage tube 12. The second drainage tube 14 is positioned such that the plurality of apertures 20 thereof are located in the right atrium 76, thereby allowing blood from the right atrium 76 to drain through the plurality of apertures 20 and into the second drainage tube 14. As noted above, in some embodiments, the plurality of apertures 20 may be located in the right ventricle in addition to or as an alternative of being positioned in the right atrium 76, thereby allowing blood from the right ventricle to drain through the plurality of apertures 20.

At or near an inlet fitting of a blood pump 80, the drainage cannula 10 may include a port 22. As described above with respect to FIGS. 1-6, port 22 may be configured to communicate with a sleeve (not shown) configured to modulate fluid flow through the second drainage tube 14. Additionally and/or alternatively, while not shown in FIG. 11, it is to be understood that a second port (in addition to port 22) may be provided, with the second port in communication with a secondary sleeve (not shown) configured to modulate fluid flow through the first drainage tube 12, as is shown and described with respect to FIGS. 7 and 8.

The pump 80 can be any centrifugal, axial, mixed, or roller pump that can produce adequate flowrates through the system. Several examples of pumps include, without limitation the TANDEMHEART pump manufactured by Cardiac Assist, Inc., the BIOMEDICUS pump manufactured by Medtronic, Inc., the ROTAFLOW pump manufactured by Jostra Medizintechnik AG, the CENTRIMAG pump manufactured by Levitronix, LLC, the SARNS DELPHIN pump manufactured by the Terumo Cardiovascular Group, the REVOLUTION pump manufactured by Cobe Cardiovascular, Inc, and others. The pump 80 can be secured to the patient, for instance with a holster 82 that holds the pump 80 with a strap or in a pocket. The holster 82 can be wrapped around the abdomen or shoulder or leg of the patient. A controller 84 may be provided for controlling the operation of the pump 80. The controller 84 may be built into the pump 80. The pump 80 further includes an outlet 86 for delivering blood to an oxygenator 88. The oxygenator 88 may be secured to the holster 82. The pump outlet 86 may be directly connected to the oxygenator 88, or the pump outlet 86 may be indirectly connected to the oxygenator 88 via a conduit or hose. The oxygenator 88 includes an oxygenation membrane or other element(s) for oxygenating blood flowing through the oxygenator 88. Oxygenated blood is delivered to an artery in the patient's body through an infusion cannula 90. While FIG. 11 illustrates the infusion cannula 90 connected to the patient's femoral artery 92, the infusion cannula in other embodiments may be connected to the patient's subclavian artery or another artery of the patient's vascular system.

In the VA ECMO system 100, the drainage cannula 10 allows the right atrial sourcing component, namely the second drainage tube 14, to drain the majority of venous flow, such as 4 liters per minute (lpm) out of a typical system flow of 5 lpm, leaving the pulmonary artery sourcing component, namely the first drainage tube 12, to drain the remaining 1 lpm.

Having described several non-limiting aspects of the drainage cannula 10 and the VA ECMO system 100, an exemplary and non-limiting method for bilateral unloading of a patient's heart using the drainage cannula 10 will now be described with continued reference to FIGS. 10-11.

In use, the drainage cannula 10 is inserted into the patient's vasculature in a percutaneous procedure prior to being connected to the other components of the VA ECMO system 100. Initially, a percutaneous entry needle (not shown) is used to access the patient's internal jugular vein 94 or the femoral vein. A guidewire, such as a guidewire having maximum diameter 0.038 in. (0.965 mm) and a minimum length of 170 cm, is inserted into the vasculature. In some aspects, the positioning of the guidewire is verified using an appropriate imaging technique. In the next step, the patient's active clotting time is checked for approximately 400 seconds.

The drainage cannula 10 may then be guided over the guidewire into the desired position within the patient's vasculature, shown in FIGS. 10 and 11. In some embodiments, an introducer (not shown) may be inserted into the first drainage tube 12 prior to guiding the drainage cannula 10 over the guidewire. In some aspects, the drainage cannula 10 may be guided into a desired position using indicia, such as a radiopaque marker located in the first distal end 72 of the first drainage tube 12 that is visualized under fluoroscopy, transthoracic echocardiography, or cineangiography. The position of the drainage cannula 10 may be guided and verified by an imaging system described in WO 2015/139031, the disclosure of which is hereby incorporated by reference in its entirety. After noting and recording the location of the drainage cannula 10, the introducer (if utilized) can be removed.

To connect the drainage cannula 10 to the blood pump 80, a wet-to-wet, or other type, of a connection is made between the drainage cannula 10 and the pump 80. After verifying the correct positioning and insertion depth of the drainage cannula 10, the drainage cannula 10 can be secured to the patient, such as by suturing with a suture wing. The patient's active clotting time is checked and confirmed to be in an approximate range of 180-220 seconds before turning on the blood pump 80 to circulate the patient's blood through the VA ECMO system 100. During use, fluid drained from the pulmonary artery 78 via the first drainage tube 10 and fluid drained from the right atrium 76 via the second drainage tube 14 flow proximally out of the drainage cannula 10 and into the blood pump 80. The blood pump 80 pumps the blood received from the drainage cannula 10 to the oxygenator 88 to oxygenate the blood, which is then returned to the patient via the infusion line 90. After use, the pump 80 may be turned off and the pump inlet and outlet may be clamped. Any sutures securing the drainage cannula 10 to the patient may be removed, and the drainage cannula 10 removed from the patient. The puncture site may then be treated and dressed. Additional details of a VA ECMO procedure are described in PCT Application Publication No. WO 2016/054543, the disclosure of which is hereby incorporated by reference in its entirety.

While the above-described embodiments pertain to a dual lumen drainage cannula for use in a VA ECMO procedure having at least a sleeve capable of modulating flow through at least one drainage tube, it is to be understood that the concept of providing an expandable lumen within another lumen so as to modulate fluid flow therethrough is equally applicable to other dual lumen cannula configurations. For example, a dual lumen cannula having a first lumen configured as an infusion tube and a second, coaxial lumen configured as a drainage tube may incorporate the features and flow modulation characteristics of the expandable lumen(s) described herein.

Furthermore, while several embodiments of a drainage cannula are shown in the accompanying figures and described hereinabove in detail, other embodiments will be apparent to, and readily made by, those skilled in the art without departing from the scope and spirit of the invention. For example, it is to be understood that this disclosure contemplates, to the extent possible, that one or more features of any embodiment can be combined with one or more features of any other embodiment. Accordingly, the foregoing description is intended to be illustrative rather than restrictive.

What is claimed is:

1. A dual lumen drainage cannula configured for use in a veno-arterial extracorporeal membrane oxygenation (VA ECMO) system, the dual lumen drainage cannula comprising:
   a first drainage tube having a proximal end, a distal end, and at least one aperture defined in at least one wall of the first drainage tube proximate to the distal end of the first drainage tube;
   a second drainage tube having a proximal end, a distal end, and at least one aperture defined in at least one wall of the second drainage tube proximate to the distal end of the second drainage tube, wherein the first drainage tube passes through the second drainage tube, and wherein the distal end of the second drainage tube is coupled to a portion of the first drainage tube between the proximal end and the distal end of the first drainage tube; and
   a sleeve positioned adjacent to an interior wall of the second drainage tube, wherein at least one wall of the sleeve is formed of a flexible material so as to be expandable and collapsible within the second drainage tube.

2. The dual lumen drainage cannula according to claim 1, further comprising a port formed on an exterior wall of the second drainage tube, wherein the port is in communication with the sleeve.

3. The dual lumen drainage cannula according to claim 2, wherein the port is located adjacent to the proximal end of the second drainage tube.

4. The dual lumen drainage cannula according to claim 2, wherein the sleeve extends from the port to the distal end of the second drainage tube.

5. The dual lumen drainage cannula according to claim 2, wherein the sleeve is sized and configured to receive at least one element therein so as to allow for expansion of the sleeve.

6. The dual lumen drainage cannula according to claim 5, wherein the at least one element is at least one flexible rod.

7. The dual lumen drainage cannula according to claim 5, wherein the at least one element is a fluid.

8. The dual lumen drainage cannula according to claim 1, further comprising a secondary sleeve positioned adjacent to an interior sidewall of the first drainage tube, wherein at least one wall of the secondary sleeve is formed of a flexible material so as to be expandable and collapsible within the first drainage tube.

9. The dual lumen drainage cannula according to claim 8, further comprising a secondary port formed on an exterior wall of the second drainage tube, wherein the secondary port is in communication with the secondary sleeve.

10. The dual lumen drainage cannula according to claim 1, wherein the at least one aperture of the first drainage tube is configured for draining blood from a pulmonary artery of a patient, and
wherein the at least one aperture of the second drainage tube is configured for draining blood from a right atrium of the patient.

11. The dual lumen drainage cannula according to claim 1, wherein the first drainage tube extends coaxially relative to the second drainage tube.

12. A veno-arterial extracorporeal membrane oxygenation (VA ECMO) system comprising:
a dual lumen drainage cannula comprising:
a first drainage tube having a proximal end, a distal end, and at least one aperture defined in at least one wall of the first drainage tube proximate to the distal end of the first drainage tube,
a second drainage tube having a proximal end, a distal end, and at least one aperture defined in at least one wall of the second drainage tube proximate to the distal end of the second drainage tube, wherein the first drainage tube passes through the second drainage tube, and wherein the distal end of the second drainage tube is coupled to a portion of the first drainage tube between the proximal end and the distal end of the first drainage tube, and
a sleeve positioned adjacent to an interior wall of the second drainage tube, wherein at least one wall of the sleeve is formed of a flexible material so as to be expandable and collapsible within the second drainage tube;
a blood pump having an inlet connected to an outlet of the dual lumen drainage cannula;
an oxygenator connected to an outlet of the blood pump; and
an infusion cannula connected to an outlet of the oxygenator and configured for insertion into the vasculature of a patient.

13. The VA ECMO system according to claim 12, wherein the dual lumen drainage cannula further comprises at least one port formed on an exterior wall of the second drainage tube, wherein the at least one port is in communication with the sleeve.

14. The VA ECMO system according to claim 12, wherein the sleeve is sized and configured to receive at least one element therein so as allow for expansion of the sleeve.

15. The VA ECMO system according to claim 14, wherein the at least one element comprises at least one flexible rod.

16. The VA ECMO system according to claim 14, wherein the at least one element comprises a fluid.

17. The VA ECMO system according to claim 16, further comprising a fluid source and a controller, wherein the fluid source is configured to automatically expand or collapse the at least one wall of the sleeve based on instructions received from the controller.

18. A method of providing veno-arterial extracorporeal membrane oxygenation (VA ECMO) of a heart, the method comprising:
providing a dual lumen drainage cannula comprising:
a first drainage tube having a proximal end, a distal end, and at least one aperture defined in at least one wall of the first drainage tube proximate to the distal end of the first drainage tube,
a second drainage tube having a proximal end, a distal end, and at least one aperture defined in at least one wall of the second drainage tube proximate to the distal end of the second drainage tube, wherein the first drainage tube passes through the second drainage tube, and wherein the distal end of the second drainage tube is coupled to a portion of the first drainage tube between the proximal end and the distal end of the first drainage tube, and
a sleeve positioned adjacent to an interior wall of the second drainage tube, wherein at least one wall of the sleeve is formed of a flexible material so as to be expandable and collapsible within the second drainage tube;
inserting the dual lumen drainage cannula into a first site in a patient's vasculature;
maneuvering the dual lumen drainage cannula through the patient's vasculature such that the distal end of the first drainage tube is at least within proximity of the patient's pulmonary artery and such that the distal end of the second drainage tube is at least within proximity of the patient's right atrium;
draining blood through the first drainage tube and the second drainage tube to a blood pump;
pumping drained blood through an oxygenator to reduce carbon dioxide content of the blood; and
delivering oxygenated blood with reduced carbon dioxide content to a second site in the patient's vasculature.

19. The method of claim 18, wherein the dual lumen drainage cannula further comprises at least one port formed on an exterior wall of the second drainage tube and configured to be in communication with the sleeve, and wherein the method comprises inserting at least one element into the sleeve via the port so as to expand the sleeve within the second drainage tube.

20. The method of claim 19, wherein inserting at least one element into the sleeve comprises one of inserting at least one flexible rod into the sleeve and inserting a fluid into the sleeve.

* * * * *